ature greater than the boiling point of product methoxysilane and less than the temperature of methanol. Under these temperature conditions rapid removal of product methoxysilanes from the reaction mixture occurs minimizing undesirable reactions which can reduce yield of the process. The described process has been found useful for the production of dimethylmethoxysilane, dimethyldimethoxysilane, and methyldimethoxysilane.

United States Patent [19]

Legrow

[11] Patent Number: 5,084,589
[45] Date of Patent: Jan. 28, 1992

[54] PROCESS FOR SYNTHESIS OF METHOXY SUBSTITUTED METHYLSILANES
[75] Inventor: Gary E. Legrow, Midland, Mich.
[73] Assignee: Dow Corning Corporation, Midland, Mich.
[21] Appl. No.: 729,955
[22] Filed: Jul. 15, 1991
[51] Int. Cl.$^5$ ............................................... C07F 7/18
[52] U.S. Cl. ................................................... 556/470
[58] Field of Search ........................................ 556/470

[56] References Cited

U.S. PATENT DOCUMENTS

| | | | |
|---|---|---|---|
| 4,228,092 | 10/1980 | Kötzsach et al. | 556/422 |
| 4,395,564 | 7/1983 | Kanner et al. | 556/470 |
| 4,518,787 | 5/1985 | Treadgold | 556/470 X |
| 4,730,074 | 3/1988 | Lewis et al. | 556/470 |
| 4,851,558 | 7/1989 | Nishida et al. | 556/47 |

OTHER PUBLICATIONS

Viswanathan et al., J. Chem. Soc. 3:487 (1968); The Synthesis and Some Properties of Methoxydimethylsilane.
Nametkin et al., Chem. Abst. 87(29): 152309s (1977) Preparation of an Organomagnesium Compound from Monochleromethyl . . . .
Nazran et al.; J. Am. Chem. Soc. 106:7267 (1984); Dimethylsilylene: Its Optical Absorption Spectrum and Reaction Kinetics.

Primary Examiner—Paul F. Shaver
Attorney, Agent, or Firm—William F. Boley

[57] ABSTRACT

The present invention is a process for the production of selected methoxysilanes in high yield. The process involves reacting methanol with a silazane at a temperature greater than the boiling point of product methoxysilane and less than the temperature of methanol. Under these temperature conditions rapid removal of product methoxysilanes from the reaction mixture occurs minimizing undesirable reactions which can reduce yield of the process. The described process has been found useful for the production of dimethylmethoxysilane, dimethyldimethoxysilane, and methyldimethoxysilane.

15 Claims, No Drawings

PROCESS FOR SYNTHESIS OF METHOXY SUBSTITUTED METHYLSILANES

BACKGROUND

The present invention is a process for the production of selected methoxysilanes in high yield. The process involves reacting methanol with a silazane at a temperature greater than the boiling point of product methoxysilane and less than the temperature of methanol. Under these temperature conditions rapid removal of product methoxysilanes from the reaction mixture occurs minimizing undesirable reactions which can reduce yield of the process. The described process has been found useful for the production of dimethylmethoxysilane, dimethyldimethoxysilane, and methyldimethoxysilane.

Several reports in the literature describe processes for the production of methoxysilanes.

Viswanathan and Van Dyke, J. Chem. Soc. 3:487, 1968, report the preparation of dimethylmethoxysilane in 97% yield by the reaction of methanol with $(Me_2SiH)S$.

Nametkin et al., Chem. Abst. 87(29):152309s, 1977, report that the reaction of dimethylchlorosilane with $MeOCH_2Cl$ and magnesium in the presence of $HgCl_2$, and Fe in THF gives a 35-76% yield of dimethylmethoxysilane.

Nazran et al., J. Am. Chem. Soc. 106:7267, 1984, report a process giving greater than 95% yield of dimethylmethoxysilane. The process involves the photolysis of dodecamethylcyclohexasilane as a source of dimethylsilylene and the subsequent reaction of the dimethylsilylene with methanol to form dimethylmethoxysilane.

Kotzsch et al., U.S. Pat. No. 4,228,0921, issued Oct. 14, 1980, describes a process for esterification of an organochlorosilane. The process comprises feeding alcohol into a chlorosilane maintained within a reaction zone without the alcohol contacting the chlorosilane in the gas phase. The esterification is performed stepwise with extraction of hydrogen chloride as it is formed. Addition of the alcohol component is through a bottom valve or by immersion of the supply conduit. The process is reported to be useful for production of dimethylmethoxysilane, dimethyldimethoxysilane, and methyldimethoxysilane.

Nashida et al., U.S. Pat. No. 4,851,558, issued July 25, 1989, report a process for the production of alkoxysilanes containing at least one hydrogen bound to the silicon atom. In the described process, chlorosilane is reacted with an alcohol in the co-presence of a solvent having a boiling point higher than and a solvent having a boiling point lower than the boiling point of the objective alkoxysilane. The process is reported capable of producing dimethylmethoxysilane, dimethyldimethoxysilane, and methyldimethoxysilane.

The objective of the present process is to produce selected methoxysilanes, in high yield, from readily available starting materials; without the use of solvents, catalyst, and other components which can create separation and disposal problems. An additional objective is to provide a high yield method for producing the described methoxysilanes, which results in a product low in chloride content. The availability of methoxysilanes with low chloride content is important, since chloride can act as poison for catalysts, for example platinum, used in reactions where the methoxysilane is an intermediate.

The methoxysilanes obtained by the instant process contain reactive methoxy groups and in some cases hydrogen and as such are useful as intermediates for preparing various organic silicon compounds or silicon functional polysiloxanes.

SUMMARY OF THE INVENTION

The present invention is a process for the production of selected methoxysilanes in high yield. The selected methoxysilanes, which can be produced by the present process, are dimethylmethoxysilane, dimethyldimethoxysilane, and methyldimethoxysilane. The process comprises contacting methanol with a silazane at a temperature greater than that of the product methoxysilane and less than the boiling point of methanol. The product methoxysilane is removed from the reactor as it is formed to minimize undesired reactions, thus improving product yield.

DESCRIPTION OF THE INVENTION

The present invention is a process for producing selected methoxysilanes in high yield. The process consists of contacting methanol with a silazane at a temperature greater than the product methoxysilane boiling point and less than the methanol boiling point.

The rational for running the described process at a temperature greater than the boiling point of the methoxysilane product and less than the boiling point of the methanol may best be understood in the context of the following reactions. When a silazane, such as tetramethyldisilazane, is reacted with methanol the following type reactions can occur:

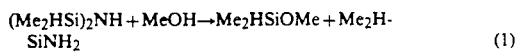

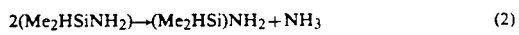

In the described process, for example, if dimethylmethoxysilane is the desired product the yield of this product can be reduced by the reaction described in equation (3). In addition, ammonia ($NH_3$) generated by the reaction described in equation (2) acts as a catalyst for the reaction of equation (3). Thus, the presence of residual ammonia in the process can further reduce product yield.

The present process reduces such undesired reactions by rapidly removing the product methoxysilanes from contact with methanol and ammonia, thus improving yield of the desired products. This rapid removal of product is accomplished by maintaining the temperature of the reactor in which the process is run above the boiling point of the product alkoxysilane to effect vaporization, and withdrawing the methoxysilane vapor from the reactor as the vapor is formed. Since the reactor is maintained below the boiling point of the methanol, minimal methanol exits the reactor in the gaseous phase. By-product ammonia also leaves the reactor as a vapor, but is separated from the product methoxysilanes in a condenser maintained at a temperature below the condensation point of the product methoxysilane, but above the boiling point of ammonia.

In a preferred embodiment of the instant invention an inert purging gas, such as nitrogen, is bubble through the liquid contained in the reactor and through the product methoxysilane collected in the condenser. The purging gas acts as a carrier to remove product methoxysilane and ammonia from the reactor and as a carrier to remove residual ammonia from the product methoxysilane collected in the condenser.

Therefore, one embodiment of the present invention is a process for the preparation of dimethylmethoxysilane. The process comprising:

(A) in a reactor containing tetramethyldisilazane delivering methanol below the surface of the tetramethyldisilazane to form a mixture.

(B) maintaining the mixture at a temperature greater than dimethylmethoxysilane boiling point and less than the methanol boiling point, to effect dimethylmethoxysilane formation and vaporization, and (C) recovering the vaporized dimethylmethoxysilane.

The reactor for the described process can be any closed vessel containing one or more ports for adding reactants to the vessel and removing product methoxysilane and by-product gases. An aliquot of tetramethyldisilazane is charged to the reactor and the reactor heated to a temperature greater than the boiling point of dimethylmethoxysilane and less than the boiling point of methanol. Heat can be provided to the reactor by standard means, for example, a heating jacket around the reactor containing a heating coil, or a heating jacket through which a heated fluid is circulated. Preferred is when the reactor is run under conditions of near atmospheric pressure and the temperature of the reactor is within the range of about 36° C. to 64° C. The process can also be run under reduced pressure to facilitate removal of gaseous product and by-product from the reactor. When the process is run under reduced pressure, the process temperature must be adjusted accordingly.

Liquid methanol is delivered beneath the surface of the heated tetramethyldisilazane to form a mixture. The method of delivering the methanol beneath the surface of the tetramethyldisilazane is not critical to the instant invention. The methanol can be delivered by, for example, a conduit extending beneath the surface of the tetramethyldisilazane or a delivery port in the bottom of the reactor. The methanol should be delivered under sufficient pressure to assure the tetramethyldisilazane does not backup into the delivery conduit or the delivery port. It is preferred that the reaction mixture be mixed to avoid localized concentrations of methanol. Mixing can be accomplished by standard methods for mixing liquids, for example, a magnetic stirrer and stir bar, a shaft driven propeller, bubbling of a carrier gas through the mixture, or a combination thereof.

The rate of delivery of methanol to the reactor is not critical and is limited only by the ability to assure adequate mixing, temperature control, and product and by-product removal.

The product dimethylmethoxysilane is removed from the reactor as it is formed. Removal of the product dimethylmethoxysilane can be via a recovery port located above the surface of the liquid contained in the reactor. Preferred is when the recovery port is located near the top of the reactor.

The vaporized product dimethylmethoxysilane is recovered from the reactor as it exits the recovery port. Recovery of the gaseous dimethylmethoxysilane is effected by reducing the temperature below the boiling point of the dimethylmethoxysilane. As previously described, ammonia is a by-product of the described process and ammonia can serve as a catalyst for undesired reactions which reduce the yield of the dimethylmethoxysilane. Therefore, it is desirable to remove ammonia from contact with the dimethylmethoxysilane as rapidly as possible. In a preferred process, the dimethylmethoxysilane and ammonia gases exiting through the recovery port of the reactor are passed through a condenser which cools the gases to a temperature below the boiling point of the dimethylmethoxysilane and above the boiling point of ammonia. The condensated dimethylmethoxysilane is collected as a liquid and the gaseous ammonia is removed from the process.

In a preferred process, an inert carrier gas is bubble beneath the surface of the liquid within the reactor to effect more efficient removal of product dimethylmethoxysilane and ammonia from the reactor. The inert carrier gas can be for example, nitrogen, argon, or helium. The preferred carrier gas is nitrogen.

It is also preferred that additional carrier gas be bubbled through the collected liquid dimethylmethoxysilane to remove any residual ammonia.

The rate with which the carrier gas is delivered to the reactor and to the collected liquid dimethylmethoxysilane is dependent upon vessel volume, quantity of mixture present, and rate of product formation. Generally, the flow rate of carrier gas should be sufficient to prevent excessive accumulation of dimethylmethoxysilane and ammonia in the reactor and accumulation of ammonia in the collector.

The described process can be run as a batch process or as a continuous process, with replenishment of the tetramethyldisilazane as it is consumed.

The present process is also useful for reacting methylhydrogencyclosilazane with methanol to form methyldimethoxysilane. The process comprises:

(A) in a reactor containing methylhydrogencyclosilazane of formula

where n is an integer from 3 to 7, delivering methanol below the surface of the methylhydrogencyclosilazane to form a mixture.

(B) maintaining the mixture at a temperature greater than methyldimethoxysilane boiling point and less than the methanol boiling point, to effect methyldimethoxysilane formation and vaporization, and (C) recovering the vaporized methyldimethoxysilane.

Into a reactor, as previously described for the production of dimethylmethoxysilane, is added an aliquot of methylhydrogencylosilazane. The reactor is heated, as previously described, to temperature greater than the boiling point of methyldimethoxysilane and less than the boiling point of methanol. The preferred temperature range, at near atmospheric pressure, is about 60° C. to 64° C.

Methanol is delivered beneath the surface of the cyclic silazane, as previously described, to form a mixture. Product methyldimethoxysilane and ammonia by-product gases are remove from the reactor, separated and collected as previously described for the process for producing dimethylmethoxysilane. The use of a carrier gas, as previously described is also preferred. The process may be run as a batch or continuous process, with the methylhydrogencyclosilazane being replenished as it is consumed.

Quite unexpectedly, the present process has been found to give near quantitative yields of dimethyldimethoxysilane when an aliquot of methanol is added to the reactor and tetramethyldisilazane is added beneath the surface of the methanol. Therefore, a process is claimed comprising:

(A) in a reactor containing methanol, delivering tetramethyldisilazane below the surface of the methanol to form a mixture.

(B) maintaining the mixture at a temperature greater than dimethyldimethoxysilane boiling point and less than the methanol boiling point to effect dimethyldimethoxysilane formation and vaporization, and (C) recovering the vaporized dimethyldimethoxysilane.

Into a reactor, as previously described for the production of dimethylmethoxysilane, is added an aliquot of methanol. The reactor is heated, by means previously described, to a temperature greater than the boiling point of dimethyldimethoxysilane and less than the boiling point of methanol. The preferred temperature range, at near atmospheric pressure, is about 28° C. to 64° C.

Tetramethyldisilazane is delivered beneath the surface of the methanol, as previously described, to form a mixture. Product dimethyldimethoxysilane and ammonia by-product gases are remove from the reactor, separated and collected as previously described for the process for producing dimethylmethoxysilane. The use of a carrier gas, as previously described, is also preferred.

The process can be run as a batch or a continuous process, with additional methanol being added to the reactor to replenish that being consumed.

The following examples are offered to facilitate understanding of the present process. These examples are not intended to be limiting on the claims herein.

EXAMPLE 1.

Dimethylmethoxysilane was produced in near quantative yield by reacting tetramethyldisilazane with methanol under conditions which allowed for quick removal of dimethylmethoxysilane from the reactor to minimize undesired reactions.

The reactor consisted of a 3-neck flask surrounded by a heating mantle and containing a magnetic stirring bar. One neck of the reactor was fitted with a dual inlet containing a thermometer and a tube for delivering an inert gas to the reactor. Both the thermometer and tube for delivering inert gas were positioned to reach near the bottom of the reactor. A second neck of the reactor was equipped with a pressure equalizing liquid addition funnel for delivering methanol to the reactor. Methanol from the addition funnel was delivered into the reactor by a tube that extended to near the bottom of the reactor. The third neck of the reactor was connected to a water-cooled condenser. The exit end of the condenser connected to a first neck of a collector consisting of a second 3-neck flask. A second neck of the collector was equipped with a tube extending to near the bottom of the collector, for delivering an inert gas to the collector. The third neck of the collector was connected to a second water cooled condenser.

One mole (133 g) of tetramethyldisilazane was added to the reactor and two moles (64 g) of dry methanol were added to the addition funnel. The tetramethyldisilazane was heated to about 50° C. with stirring. Nitrogen gas flow, as an inert carrier, was initiated in both the reactor and the collector. The methanol was added dropwise from the addition funnel to the reactor. At completion of addition of the methanol, the reactor was essentially empty. The product in the collector weighed 169.8 g (95% of theoretical yield of product). Gas liquid chromotography, using a mass spectrometer as detector (GC/MS), of the product showed it to be 97.4% dimethylmethoxysilane and 2.6% dimethyldimethoxysilane.

EXAMPLE 2.

The effect of adding tetramethyldisilazane to methanol was evaluated. The reaction was run similar to that described in Example 1, except that 3.0 mole (96 g) of methanol was placed in the reactor and 1.0 mole (133 g) of tetramethyldisilazane was added to the addition funnel. The methanol was heated to 50° C. stirred, and the tetramethyldisilazane added dropwise to the reactor. A nitrogen gas purge was employed, as described for Example 1.

GC/MS analysis of the liquid retained in the collector after about 50% of the tetramethyldisilazane had been added showed only the presence of methanol and dimethyldimethoxysilane. No dimethylmethoxysilane was detected.

What is claimed is:

1. A process for preparation of dimethylmethoxysilane, the process comprising:
   (A) in a reactor containing tetramethyldisilazane, delivering methanol below the surface of the tetramethyldisilazane to form a mixture,
   (B) maintaining the mixture at a temperature greater than dimethylmethoxysilane boiling point and less than the methanol boiling point, to effect dimethylmethoxysilane formation and vaporization, and
   (C) recovering the vaporized dimethylmethoxysilane.

2. A process according to claim 1, where the temperature is within a range of about 36° C. to 64° C.

3. A process according to claim 1, where recovering the vaporized dimethylmethoxysilane is facilitated by delivering an inert gas beneath the mixture surface as a carrier for removal of the vaporized dimethylmethoxysilane and vaporized by-product ammonia from the mixture.

4. A process according to claim 3, where the inert gas vaporized dimethylmethoxysilane, and vaporized by-product ammonia are passed to a cooling condenser maintained at a temperature less than the dimethylmethoxysilane boiling point and greater than the by-product ammonia boiling point, where the vaporized dimethylmethoxysilane is condensed to liquid dimethylmethoxysilane.

5. A process according to claim 4, where residual by-product ammonia is removed from the liquid dimethylmethoxysilane by bubbling of additional carrier gas through the liquid dimethylmethoxysilane.

6. A process for preparation of dimethyldimethoxysilane, the process comprising:
   (A) in a reactor containing methanol, delivering tetramethyldisilazane below the surface of the methanol to form a mixture.
   (B) maintaining the mixture at a temperature greater than dimethyldimethoxysilane boiling point and less than the methanol boiling point, to effect dimethyldimethoxysilane formation and vaporization, and
   (C) recovering the vaporized dimethyldimethoxysilane.

7. A process according to claim 6, where the temperature is within a range of about 28° C. to 64° C.

8. A process according to claim 6, where recovering the vaporized dimethyldimethoxysilane is facilitated by delivering an inert gas beneath the mixture surface as a carrier for removal of the vaporized dimethyldimethoxysilane and vaporized by-product ammonia from the mixture.

9. A process according to claim 8, where the inert gas, vaporized dimethyldimethoxysilane, and vaporized by-product ammonia are passed to a cooling condenser maintained at a temperature less than the dimethyldimethoxysilane boiling point and greater than the by-product ammonia boiling point, where the vaporized dimethyldimethoxysilane is condensed to liquid dimethyldimethoxysilane.

10. A process according to claim 9 where residual by-product ammonia is removed from the liquid dimethyldimethoxysilane by bubbling of additional carrier gas through the liquid dimethyldimethoxysilane.

11. A process for preparation of methyldimethoxysilane, the process comprising:
(A) in a reactor containing a methylhydrogencyclosilazane of formula (HMeSiNH)$_n$.

where n is an integer from 3 to 7, delivering methanol below the surface of the methylhydrogencyclosilazane to form a mixture.
(B) maintaining the mixture at a temperature greater than methyldimethoxysilane boiling point and less than the methanol boiling point to effect methyldimethoxysilane formation and vaporization, and
(C) recovering the vaporized methyldimethoxysilane.

12. A process according to claim 11, where the temperature is within a range of about 60° C. to 64° C.

13. A process according to claim 11, where recovering the vaporized methyldimethoxysilane is facilitated by delivering an inert gas below the mixture surface as a carrier for removal of the vaporized methyldimethoxysilane and vaporized by-product ammonia from the mixture.

14. A process according to claim 13, where the inert gas, vaporized methyldimethoxysilane, and vaporized by-product ammonia are passed to a cooling condenser maintained at a temperature less than the methyldimethoxysilane boiling point and greater than the by-product ammonia boiling point, where the vaporized methyldimethoxysilane is condensed to liquid methyldimethoxysilane.

15. A process according to claim 14, where residual by-product ammonia is removed from the liquid methyldimethoxysilane by bubbling of additional carrier gas through the liquid methyldimethoxysilane.

* * * * *